(12) United States Patent
Sixto, Jr. et al.

(10) Patent No.: US 9,987,061 B2
(45) Date of Patent: Jun. 5, 2018

(54) IMPLANT WITH SUSPENDED LOCKING HOLES

(71) Applicant: Biomet C.V., Gibraltar (GI)

(72) Inventors: Robert Sixto, Jr., Miami, FL (US); Jose Luis Francese, Miami Springs, FL (US); Juergen A. Kortenbach, Miami Springs, FL (US); Andrea Suarez, Miami, FL (US)

(73) Assignee: Biomet C.V., Warsaw, IN (US)

( * ) Notice: Subject to any disclaimer, the term of this patent is extended or adjusted under 35 U.S.C. 154(b) by 405 days.

(21) Appl. No.: 14/166,058

(22) Filed: Jan. 28, 2014

(65) Prior Publication Data

US 2015/0209091 A1  Jul. 30, 2015

(51) Int. Cl.
*A61B 17/80* (2006.01)

(52) U.S. Cl.
CPC ...... *A61B 17/8057* (2013.01); *A61B 17/8028* (2013.01); *A61B 17/8052* (2013.01)

(58) Field of Classification Search
CPC ............ A61B 17/7059; A61B 17/8042; A61B 17/8047; A61B 17/8033; A61B 17/80; A61B 17/8052; A61B 17/8057; A61B 17/8061; A61B 17/809
USPC ....................................... 606/70–71, 280–299
See application file for complete search history.

(56) References Cited

U.S. PATENT DOCUMENTS

| 23,409 | A | * | 3/1859 | Thom | F16B 25/00 411/411 |
|---|---|---|---|---|---|
| 3,695,259 | A | | 10/1972 | Yost | |
| 4,838,252 | A | | 6/1989 | Klaue | |
| 5,002,544 | A | * | 3/1991 | Klaue | A61B 17/80 606/280 |
| 5,015,248 | A | | 5/1991 | Burstein et al. | |
| 5,022,277 | A | * | 6/1991 | Shaffer | F16H 25/2233 74/424.9 |
| 5,053,036 | A | | 10/1991 | Perren et al. | |
| 5,151,103 | A | | 9/1992 | Tepic et al. | |
| 5,474,553 | A | | 12/1995 | Baumgart | |
| 5,616,144 | A | * | 4/1997 | Yapp | A61B 17/7059 606/280 |
| 5,702,396 | A | | 12/1997 | Hoenig et al. | |
| 5,709,686 | A | | 1/1998 | Talos et al. | |
| 5,733,287 | A | * | 3/1998 | Tepic et al. | 606/69 |
| 5,741,258 | A | | 4/1998 | Klaue et al. | |
| 5,741,259 | A | | 4/1998 | Chan | |
| 5,749,872 | A | | 5/1998 | Kyle et al. | |
| 5,772,662 | A | * | 6/1998 | Chapman | A61B 17/72 606/280 |

(Continued)

*Primary Examiner* — Tatiana Nobrega
*Assistant Examiner* — Jessica Weiss
(74) *Attorney, Agent, or Firm* — Schwegman Lundberg & Woessner, P.A.

(57) ABSTRACT

A plate is provided with feet located laterally of adjacent compression screw holes and absent from about threaded locking holes so as to suspend the plate segment having the threaded locking holes from over the bone. This forces a minimum gap between the threaded holes and the bone, and allows the plate thereat to deflect under loads that can be practically delivered by the locking screws. By allowing the plate to deflect, the threads on the head of the locking screw can be aligned, or timed, with the threads of the threaded plate hole to reduce the required torque to insert the locking screw into the locking hole and the bone.

20 Claims, 4 Drawing Sheets

(56) References Cited

U.S. PATENT DOCUMENTS

| | | | |
|---|---|---|---|
| 5,810,823 A | 9/1998 | Klalue et al. | |
| 5,938,664 A | 8/1999 | Winquist et al. | |
| 5,954,722 A | 9/1999 | Bono | |
| 5,968,047 A * | 10/1999 | Reed | A61B 17/80 606/280 |
| 6,022,352 A | 2/2000 | Vandewalle | |
| 6,077,266 A | 6/2000 | Medoff | |
| 6,096,040 A | 8/2000 | Esser | |
| 6,129,730 A * | 10/2000 | Bono | A61B 17/8047 606/271 |
| 6,183,475 B1 | 2/2001 | Lester et al. | |
| 6,183,476 B1 | 2/2001 | Gerhardt et al. | |
| 6,206,881 B1 | 3/2001 | Frigg et al. | |
| 6,228,085 B1 | 5/2001 | Theken et al. | |
| 6,306,136 B1 | 10/2001 | Baccelli | |
| 6,309,393 B1 * | 10/2001 | Tepic | A61B 17/80 606/280 |
| 6,322,562 B1 | 11/2001 | Wolter | |
| 6,364,882 B1 | 4/2002 | Orbay | |
| 6,440,135 B2 | 8/2002 | Orbay et al. | |
| 6,454,770 B1 | 9/2002 | Klaue | |
| 6,527,776 B1 | 3/2003 | Michelson | |
| 6,592,578 B2 | 7/2003 | Henniges et al. | |
| D479,331 S | 9/2003 | Pike et al. | |
| 6,669,701 B2 | 12/2003 | Steiner et al. | |
| 6,786,909 B1 * | 9/2004 | Dransfeld | A61B 17/8052 606/280 |
| 7,128,744 B2 | 10/2006 | Weaver et al. | |
| 5,053,036 C1 | 4/2007 | Perren et al. | |
| 7,867,261 B2 | 1/2011 | Sixto, Jr. et al. | |
| 7,951,176 B2 * | 5/2011 | Grady, Jr. | A61B 17/746 606/280 |
| 7,951,178 B2 * | 5/2011 | Jensen | A61B 17/8057 606/291 |
| 8,197,521 B2 | 6/2012 | Sixto, Jr. et al. | |
| 8,491,643 B2 * | 7/2013 | Lauryssen | A61B 17/7059 606/280 |
| 8,496,690 B2 | 7/2013 | Sixto et al. | |
| 8,795,340 B2 * | 8/2014 | Weiman | A61B 17/7059 606/280 |
| 8,808,333 B2 * | 8/2014 | Kuster | A61B 17/74 606/280 |
| 8,834,532 B2 * | 9/2014 | Velikov | A61B 17/80 606/280 |
| 2004/0116930 A1 * | 6/2004 | O'Driscoll | A61B 17/8061 606/281 |
| 2005/0080421 A1 * | 4/2005 | Weaver | A61B 17/8057 606/282 |
| 2007/0088360 A1 * | 4/2007 | Orbay | A61B 17/8057 606/287 |
| 2007/0260244 A1 | 11/2007 | Wolter | |
| 2008/0051786 A1 * | 2/2008 | Jensen | A61B 17/8057 606/86 A |
| 2009/0118769 A1 * | 5/2009 | Sixto, Jr. | A61B 17/8061 606/280 |
| 2009/0312803 A1 * | 12/2009 | Austin | A61B 17/8014 606/305 |
| 2010/0004691 A1 * | 1/2010 | Amato | A61B 17/80 606/280 |
| 2010/0030276 A1 * | 2/2010 | Huebner | A61B 17/8061 606/280 |
| 2010/0121382 A1 * | 5/2010 | Weiman | A61B 17/7059 606/264 |
| 2010/0131012 A1 * | 5/2010 | Ralph | A61B 17/80 606/280 |
| 2010/0131013 A1 * | 5/2010 | Ralph | A61B 17/80 606/286 |
| 2010/0211118 A1 * | 8/2010 | Christen | A61B 17/8635 606/312 |
| 2011/0004252 A1 * | 1/2011 | Velikov | A61B 17/80 606/280 |
| 2011/0071573 A1 * | 3/2011 | Sixto | A61B 17/8014 606/286 |
| 2012/0059424 A1 * | 3/2012 | Epperly | A61B 17/8061 606/281 |

* cited by examiner

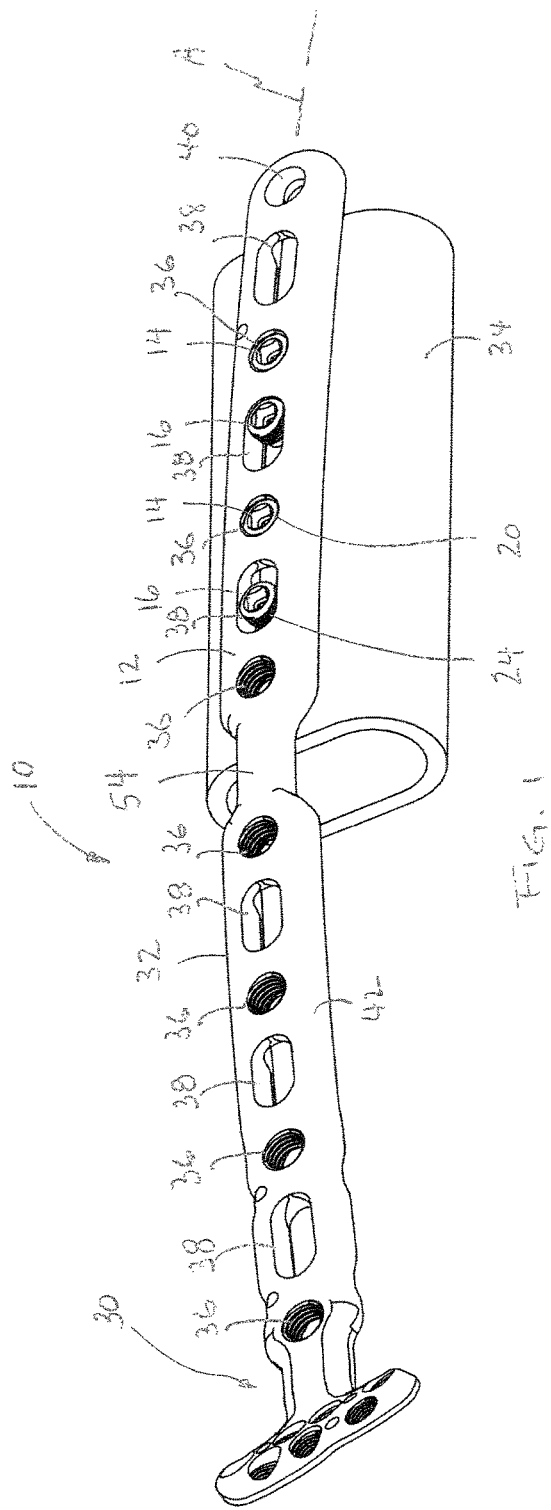
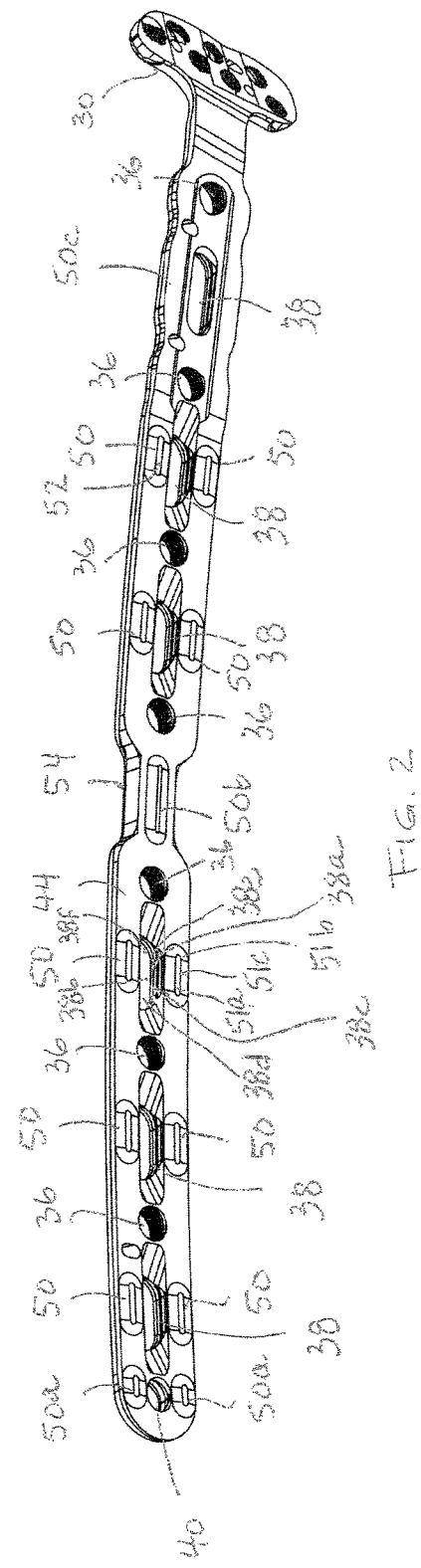
FIG. 1
FIG. 2

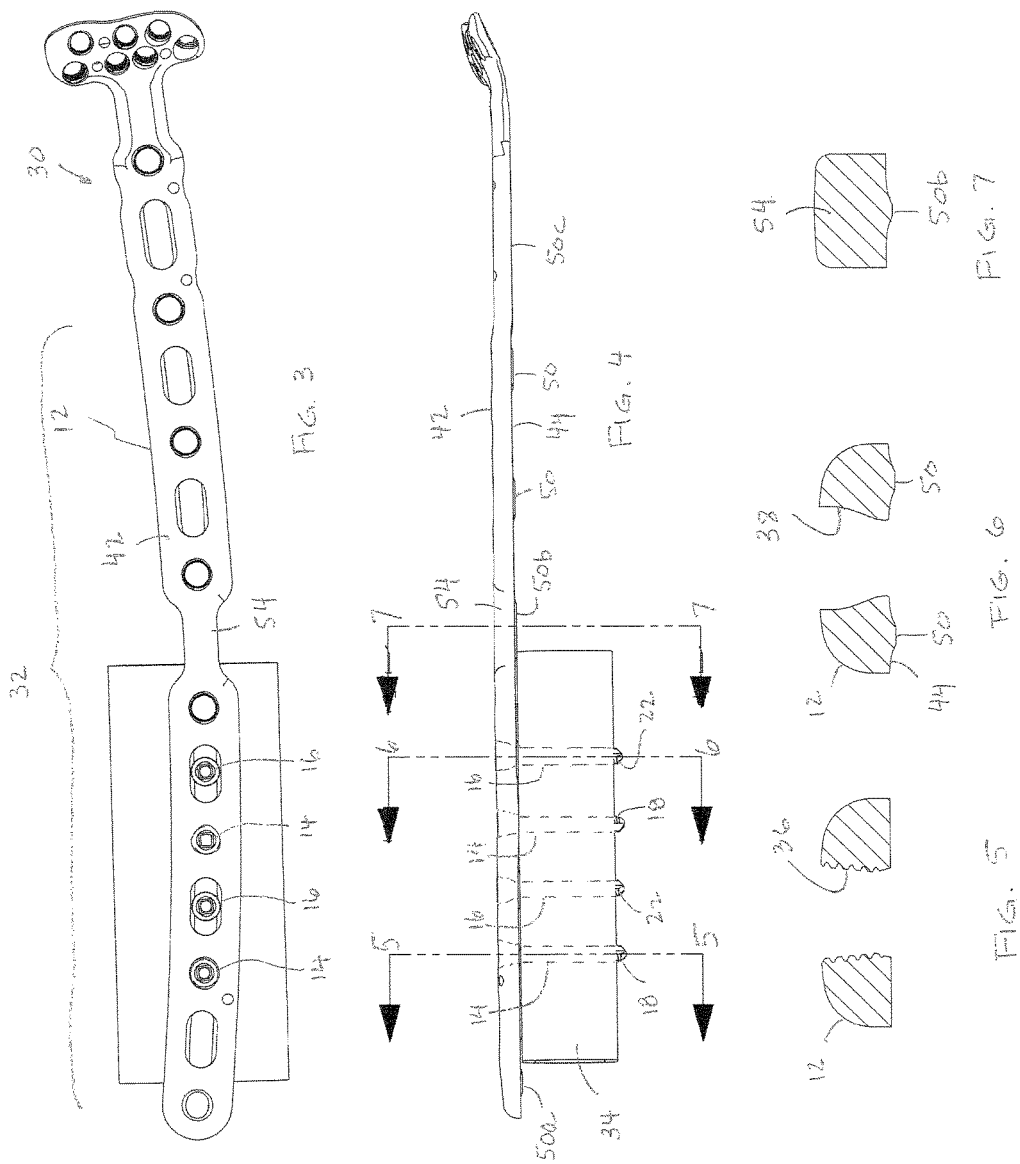

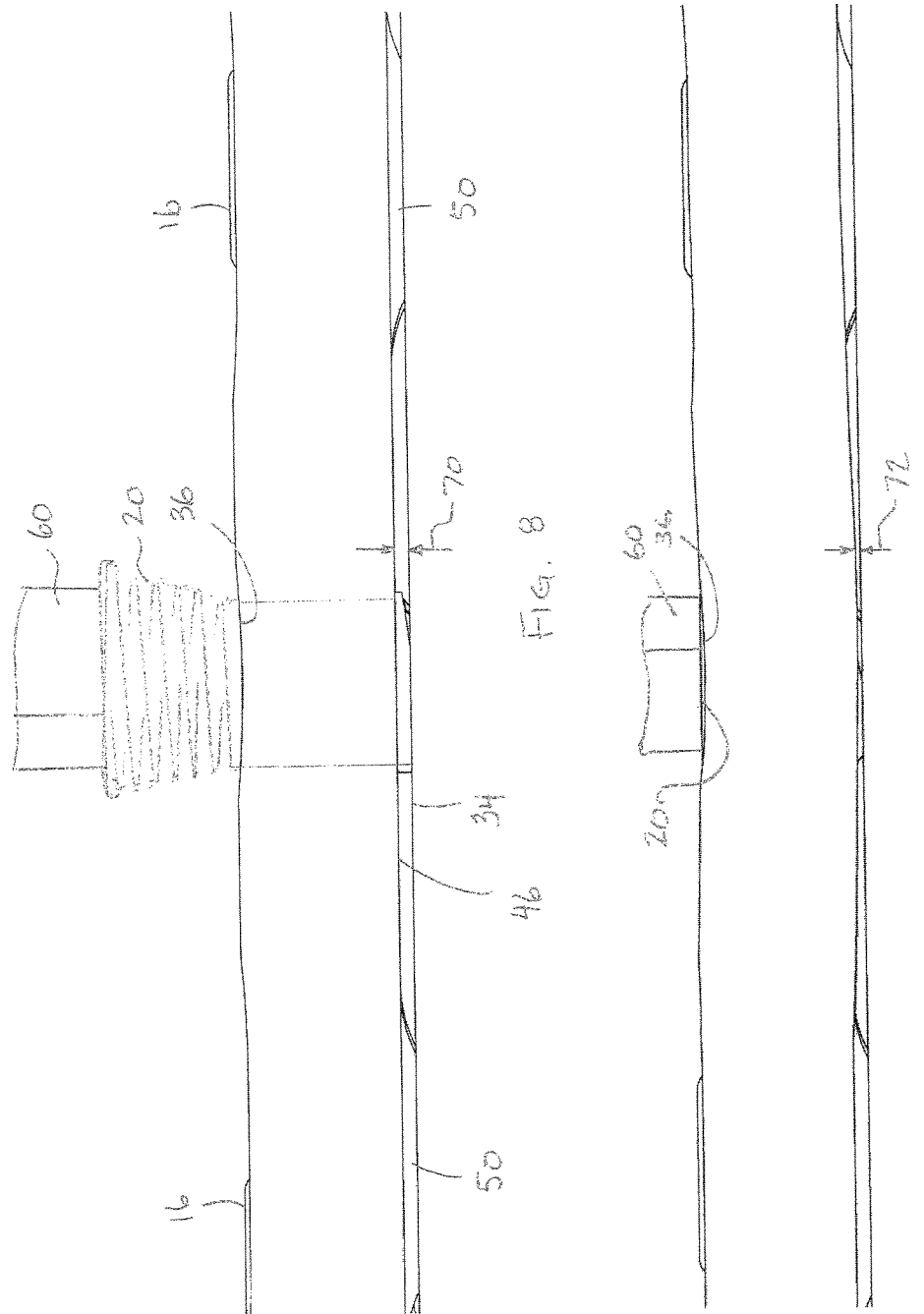

IMPLANT WITH SUSPENDED LOCKING HOLES

BACKGROUND

1. Field

The present disclosure relates to bone plates. More specifically, the present disclosure relates to plates for implantation on long bones, and the structure of the plates that facilitates the implantation of the plates on the bone.

2. State of the Art

Bone plates are implantable plates secured to a bone with bone screws that provide stabilization to a bone while the bone undergoes a healing process. The bone screws may be either compression screws or locking screws. Compression screws have a threaded shaft, but a non-threaded head portion. As the compression screw is advanced through the plate hole and into the bone, the head portion of the screw provides a compressive force against the plate to stabilize the plate against the bone. Locking screws have a threaded shaft as well as a threaded head portion. When the locking screw is inserted through the bone plate, the head portion locks relative to the bone plate to provide a secure integrated coupling between the plate and screw.

Locking screws have a significant problem caused by the fact that they have two threads: the shaft thread and the head thread. When the user begins to install the screw into the bone, the rotational position of the head thread is bound by the pitch of the shaft thread. Assuming limited positional freedom with the implant, the timing of the head thread and engagement angle of the head thread with the threads of the screw hole in the plate ('plate threads') is then, for all practical purposes, fixed. When the head of the screw begins to engage the plate it is possible that it will be rotationally aligned with the plate threads. However, more often, as the screw head enters the screw hole, the thread in the head of the screw is not rotationally aligned to threadedly engage the plate thread and is thus off from a timing perspective.

It is common for plate holes and locking screws to use a double or triple thread. With, for example a triple lead thread such holes and screws have thread starts at 120° intervals. This allows a triple lead thread to be off from the thread start of the plate by a rotational angle by in the range of 1 to 119 degrees. As the misalignment between the screw head thread and plate thread increases from approximately 1 to 60 degrees, the thread crest and plate minor diameter increasingly interfere with each other. As the interference increases so does the amount of energy needed to install the screw. The maximum interference occurs at 60 degrees and then as the misalignment continues to increase from 60 to 119 degrees, the interference recedes. The energy to install triple lead screws requires a minimum torque for installation both at zero and one hundred and twenty degrees, where there is no interference.

Thus, the energy required to install a screw is minimized when the screws are timed so that the threads are aligned. In distinction, if the threads of the screw head and the plate threads are rotationally offset so that there is a misalignment between the threads, the amount of energy required to install the screw increases.

Recently, there has been an emphasis to deliver products in a sterile disposable format. The ePAK™ system from Biomet, described in detail in U.S. Pat. No. 8,496,690, which is hereby incorporated by reference herein in its entirety, is a disposable single indication orthopedic trauma surgical kit. The system includes a single bone plate adapted for a use on a bone of a patient's extremity. The bone plate has a plurality of fastener holes. Initial versions of the system also included a plurality of fasteners of a common size, each with a head and a shaft. The screw heads are adapted to interface with the fastener holes. The system also includes a disposable torque driver adapted to engage the fastener heads, and a drill, a guide, and a depth gauge, each of which is disposable. All of the foregoing components are contained in a sterile sealed container.

In other orthopedic trauma surgical systems designed for re-sterilization and multiple use, different diameters screws have been provided, as well as different size screw drivers provided for the different size screws. This is because there is a variation in the energy needed to install different diameter screws. However, with the ePAK™ system, a driver represents a significant part of the cost of the system. For this reason it would be difficult and wasteful to deliver more than one driver in each surgical kit. Thus it is a practical requirement that a single driver be provided with the ePAK™ system for driving screws of two or more different sizes, such as both 2.7 mm and 3.5 mm screws. However, the energy required to install larger screws than originally anticipated for use with the provided driver may exceed the 1 to 17 in-lbs torque that the current driver is adapted to comfortably deliver. While a driver tip is able to engage the various screws that can be offered, the insertion thereof requires the user to apply greater torque than can be comfortably delivered. Also, driving smaller diameter screws with a larger driver than currently provided when the screws threads between plate hole and screw head are not aligned may cause binding of the screw and may allow the application of too much torque and consequent friction welding of the screw to the plate, irreversibly preventing screw removal from the plate.

SUMMARY

A bone plate system is provided with a metal bone plate having a threaded locking hole and at least two compression holes provided on longitudinally opposite sides of the threaded plate holes. The system also includes a locking screw for insertion through the threaded plate hole and at least two compression screws for insertion through the compression holes. The bone plate system may be provided with a driver for driving the compression screws and the locking screw through the plate holes, into the underlying bone, and into contact with and/or engagement with the plate. In order to minimize the amount of energy needed for installing locking screws in the threaded plate hole, the head and shaft of the locking screws are constructed to have a similar if not exactly the same pitch. This ensures that the implant is not being forced in one direction or the other due to travel differences per revolution of the screw. In accord with another preferred aspect of the bone plate, the bone plate is constructed to allow a portion of the plate defining the threaded plate hole to be slightly deflected toward the bone by a distance up to the thread pitch as the driver drives the locking screw into the threaded plate hole.

More particularly, normally, anatomical irregularities ensure that a gap exists between the implant and the bone. Soft tissue such as ligaments or muscle prop up the plates and are easily compressed by the forces exerted as the screws are installed. Unfortunately, in some instances such as on the volar aspect of the radius, the soft tissues are typically elevated by the surgeon and the bone is surprisingly flat. This causes the plate to rest directly on the bone and prevents movement of the plate relative to the bone, particularly after the compression screws are installed. If the threads in the screw head are not aligned with the threaded plate hole, the threads may bind resulting in extremely high installation torques. Alternatively, the screw may be prevented from seating in the plate resulting in a raised head that may irritate tissue. Moreover, the screw may be stripped from engagement within the bone resulting in compromised fixation and support.

The plate portion with locking holes is allowed to deflect by displacing it from and suspending it over the bone by adding feet on the bottom aspect of the bone plate adjacent the compression holes to force a minimum gap between the locking holes and the bone. The feet suspend the plate segment between the feet so that it is able to deflect under loads that can be practically delivered by the driver. That is, deformation under such loads displaces the plate segment so that the threaded locking screw head can be aligned with the threads of the threaded plate hole; i.e., so that the threaded screw head can be timed with the plate hole. This significantly reduces the required torque for implanting the screw in the bone. As a result, different diameter screws can be installed with the single driver.

The feet are preferably designed to prevent the implant from rocking or pivoting due to installation torques that may be present on either side of the feet. If the feet are not appropriately sized, the plate may shift position during non-locking screw installation.

BRIEF DESCRIPTION OF THE DRAWINGS

FIG. 1 is a perspective top side view of a bone plate according to an embodiment herein, shown relative to a schematic partial bone.

FIG. 2 is a perspective bottom view of the bone plate of FIG. 1.

FIG. 3 is a top view of the bone plate and schematic partial bone of FIG. 1.

FIG. 4 is a side elevation of the bone plate and schematic partial bone of FIG. 1.

FIG. 5 is a cross-section view across line 5-5 in FIG. 4, shown with locking screw removed.

FIG. 6 is a cross-section view across line 6-6 in FIG. 4, shown with compression screw removed.

FIG. 7 is a cross-section view across line 7-7 in FIG. 4.

FIG. 8 is an enlarged view of the bone plate at a locking plate hole as a head of the locking screw initially engages the threaded plate hole.

FIG. 9 is an enlarged view of the bone plate at the locking plate hole as a head of the locking screw deforms the plate at the threaded plate hole to allow timing of the threads between the head and the platehole.

DETAILED DESCRIPTION OF THE PREFERRED EMBODIMENTS

Figure 10:
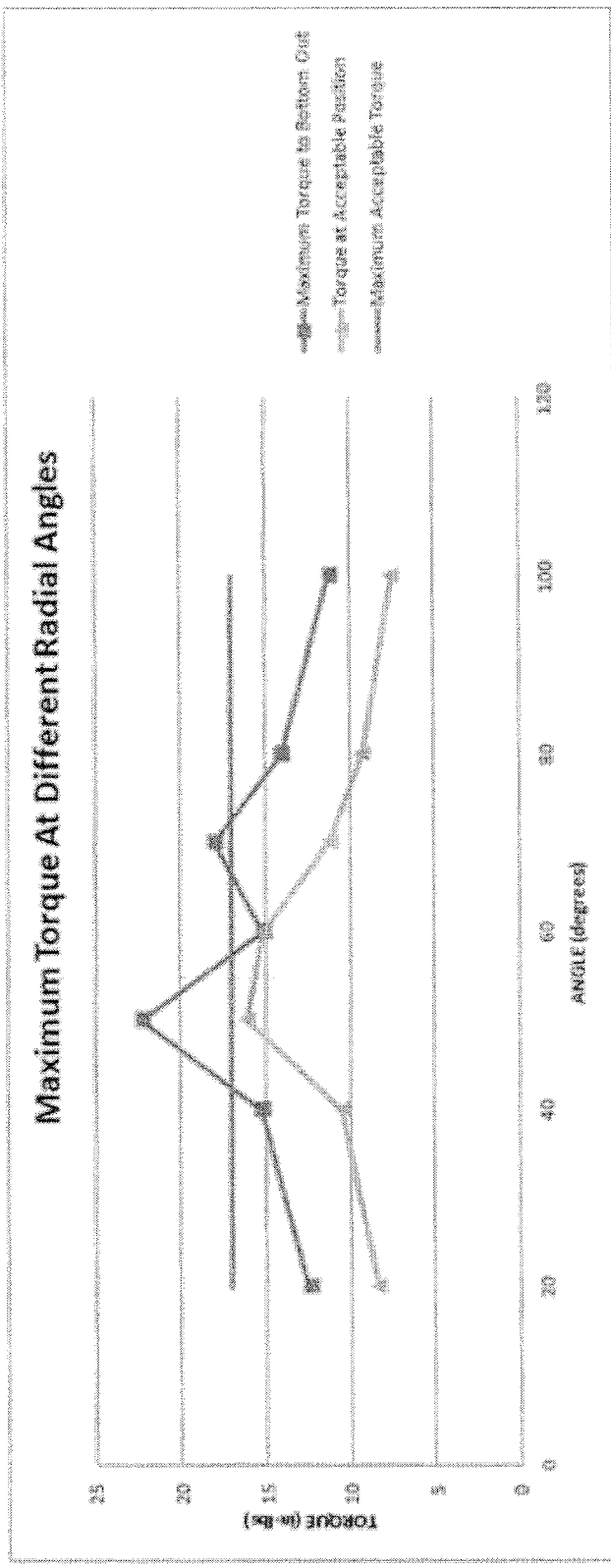
FIG. 10 is a graph illustrating the maximum torque at different radial angles for inserting a locking screw head into a threaded plate hole with and without the features of the preferred embodiments.

Turning now to FIGS. 1 to 4, a bone plate system 10 is shown. The system 10 includes a bone plate 12, one or more locking screws 14, and optionally one or more compression screws 16. The plate is preferably made from titanium. The locking screws 14 are preferably made from titanium and have a threaded shaft 18 (FIG. 4) as well as a threaded head 20 (FIG. 1). The threads of the shaft 18 and head 20 are of a common pitch. The compression screws 16 are preferably made from titanium and have a threaded shaft 22 (FIG. 4), but a head 24 that is adapted to non-threadedly engage with a non-threaded portion of a hole in the bone plate; such head 24 may be non-threaded or may include a non-threaded portion at which the head applies compression. Plates and screws of other materials may also be employed. The bone plate system 10 may be provided with a driver 60 (shown in FIG. 8), as well as a drill, a guide, and a depth gauge, all of which may be packaged together as a single-use surgical kit, with the tools being disposable. All of the foregoing kit components can be contained in a sterile sealed container.

The exemplar plate 12 shown includes a metaphyseal portion 30 for placement at the volar side of the distal radius, and a diaphyseal portion 32 for extension along the diaphysis of the radius bone 34. The bone plate 12 includes a plurality of threaded plate holes 36 and non-threaded plate holes 38, 40. The non-threaded plate holes can be both oblong, as at 38, as well as circular in form, as shown at 40. The holes are shown in an alternating arrangement of threaded holes 36 and non-threaded oblong holes 38, with the circular, non-threaded hole 40 at the end of the plate, but can be otherwise provided within the plate. By way of example, multiple non-threaded holes 38 may be provided between each of the threaded holes 36. The holes are preferably arranged along a longitudinal axis A of the plate 12.

The plate 12 includes an upper surface 42, and an opposite lower surface 44 that faces the bone 34, with the threaded and non-threaded holes 36, 38, 40 extending between the upper and lower surfaces 42, 44. In accord with a preferred aspect of the described embodiment, the plate 12 is constructed to displace the lower surface of the plate at the plate segment defining and surrounding preferably each threaded plate hole 36 away from the bone by a distance corresponding preferably at least up to the thread pitch of the head 20 of the locking screw 14. Where single lead threads are provided to the head 20 of the screw 14 and plate hole 36, the distance of displacement preferably corresponds to up to at least the thread pitch. Where double lead threads are provided to the head 20 of the screw and plate hole 36, the distance preferably corresponds to up to at least one half of the thread pitch. Where triple lead threads are provided to the head 20 of the screw and plate hole 36, the distance preferably corresponds to up to at least one third of the thread pitch.

The plate segment 46 of the lower surface 44 of the plate at the threaded hole 36 is preferably displaced from and suspended over the bone 34 by adding feet 50 on the bottom aspect of the bone plate 12 on longitudinally opposite sides of the threaded hole 36. The feet are preferably in the form of narrow, longitudinally and laterally tapered rails that extend in the longitudinal direction, and their tapered structure is adapted to dig slightly into the bone. By slightly engaging into the bone, the shape provides more stability on a bone that may have a shifting contour. Alternative structure for the feet include studs, bumps, spikes, or non-tapered ridges, although the configuration shown and described is preferred for the reasons provided herein.

The feet are provided at the lateral sides of the plate adjacent the non-threaded compression holes 38, 40 that are located adjacent to and on longitudinally opposite sides of the threaded locking screw hole. Importantly no foot extends or feet extend longitudinally with or laterally at or adjacent the threaded holes 36 so that the plate can deflect toward the bone at the threaded holes. As such, the feet 50 force a minimum gap between the plate surrounding the location of the threaded hole 36 and the bone 34 by suspending the plate segment 46 between the feet 50 so that it is able to deflect in the longitudinal direction under loads that can be practically delivered by the driver to the locking screws. The longitudinal distance between the feet 50 can be adjusted to modulate the spring rate of the suspended plate segment 46 in order to reduce the force necessary to deflect the plate the necessary distance to allow locking the locking screw to the threaded hole with a relatively low installation torque. For locking screw holes specifically adapted to receive 2.7 mm diameter locking screws, the feet are preferably longitudinally displaced apart by approximately 11±2 mm. For locking screw holes specifically adapted to receive 3.5 mm diameter locking screws, the feet are preferably longitudinally displaced apart by approximately 22±4 mm. However, it is possible, as in the preferred embodiment, that the locking screw holes are adapted to receive both 2.7 mm and 3.5 mm locking screws within the same locking holes; in such plate the preferred longitudinally displacement for the feet is approximately 11-22±4 mm.

In addition, the minimum size of the feet 50 provided on opposing lateral sides of each of the non-threaded holes 38, 40 is preferably defined by the size of the non-locking holes; at the larger oblong holes 38 the feet are larger, and at the relatively smaller round holes 40 the feet 50 are smaller. The non-locking holes 38, 40 will be subject to force by the compression screws 16 and cause the plate to be forced toward the bone 34 under compressive loads of the compression screw. The feet 50 are appropriately sized to support the compressive loads and provide plate stability. In addition, the feet 50 preferably do not have a size that exceeds the longitudinal dimension of the non-locking hole to which it is laterally adjacent. Referring to FIG. 2, in accord with a preferred embodiment, the feet 50 lateral of the oblong compression holes 38 are configured such that each foot end 51a, 51b coincides with (or substantially coincides with) an end of the straight sidewall portion 38a of the oblong compression hole 38. More particularly, the straight sidewall portion 38a is coextensive with a straight portion 38b of the oblong compression hole 38. The straight portion 38b includes a first end 38c that extends into a first curved end portion 38d and a second end 38e that extends into an opposing second curved end portion 38f. Each foot 50 at the compression hole has longitudinal bone contacting portion 51i defined between first and second foot ends 51a, 51b. The first foot end 51a substantially coincides with the first end 38d of the straight portion 38b and the second foot end 51b substantially coincides with the second end 38e of the straight portion 38b. This allows the feet to properly support and suspend the plate at the non-locking holes while providing a maximum distance to the portion of the plate that is suspended between the non-locking on the opposing longitudinal sides of the locking holes, while further preventing the plate from deflecting or moving above the foot upon off-centered insertion of a compression screw into the oblong compression hole. In addition, by otherwise minimizing the foot size, the longitudinal distance between the feet at two different compression holes is increased to thereby reduced to the bending load required to deflect the plate in the longitudinal direction toward the bone at the locking plate hole therebetween.

The feet 50 are preferably designed to prevent the implant from rocking or pivoting due to installation torques that may be present on either side of the feet. As indicated, if the feet are not appropriately sized, then the plate may shift position during non-locking screw 16 installation. The feet 50 have a relatively small contact area that may slightly sink into the bone 34 or cause depressions therein that stabilize the plate on the bone. To that end, the feet 50 preferably taper laterally and longitudinally toward a bone contacting end 52 (FIGS. 2 and 6). In addition, feet may be provided at other locations of the plate in order to maintain a relatively common height of the plate relative to the bone surface for additional stability. For example, feet 50a may be provided surrounding round compression hole 40, which is located adjacent an oblong compression hole 38 and at the end of the plate. Referring to FIGS. 4 and 7, as yet another example, a single foot 50b may be longitudinally provided along the bottom aspect of a bridge section 54 of the plate even though it is not located laterally relative to a compression hole. As yet even another example, the lower aspect of the metaphyseal portion of the plate may be provided with uninterrupted lateral rails 50c that extend about both the locking holes and the compression holes or, conversely stated, a raised central longitudinally recess at the lower aspect of the plate, which provides a substantial evenness and uniformity to the lateral lower aspect thereof. In this case, given that the metaphysis is not planar, there is often some space between the plate and that is naturally provided that may displace the plate segment defining the locking plate holes from the bone, and also allow the plate to undergo some deflection toward the bone so that misaligned threads can be timed to effect a reduction in torque to acceptable levels.

Referring to FIGS. 5 and 6, it is seen that a cross-section through the plate at the threaded locking holes 36 provides a similar cross-sectional area to a cross-section through the plate at the non-threaded compression hole 38. The primary difference is the provision of the very small feet 50 (in cross-sectional area) at the lower surface 44 of the plate at the compression hole 38.

With the provision of the feet at the bottom aspect of the plate, the plate is sufficiently raised to allow the plate to deform under loads to displace the plate so that the threaded locking screw head can be aligned with the threads of the threaded plate hole; i.e., so that the threaded screw head can be timed with the plate hole. In accord with one example of using the system, a plate is provided having a series of compression plate holes and multiple triple lead threaded plate holes having a 1.7 mm pitch, each of the threaded plate holes being located between two of the compression plate holes. Also provided are compression screws, and at least one first locking screws with a head having a triple lead thread with a 1.7 mm pitch and a 2.7 mm diameter threaded shaft and at least one second locking screw with head having a triple lead thread with a 1.7 mm pitch and a 3.5 mm diameter threaded shaft. A common driver is provided for all of the compression screws and locking screws. The plate is seated on the bone. The feet displace the locking hole from the bone by approximately 0.7 mm. The driver is used to first couple the plate to the bone with the compression screws. Referring to FIG. 8, the force of the compression screws 16 on the plate 12 cause the feet 50 to dig slightly into the bone 34 approximately 0.1 mm, leaving a space at 70 of 0.6 mm between the lower surface 44 of the plate surrounding the threaded locking hole 36 and the bone 34. The same driver 60 is then used to start inserting the first locking screw through the plate and into a pre-drilled pilot hole in the bone. Turning to FIG. 9, if the screw head 20 reaches the plate hole 36 and the threads are not timed (that is, the threads on each are not aligned), pressure is applied to the driver 60 to deflect the suspended plate segment 46 that defines the threaded locking hole 36, which is raised on the feet over the bone 34, toward the bone. A deflection 72, generally no more than 0.4-0.5 mm and at most 0.6 mm for the stated thread pitch, offsets the pitch of the thread of the plate hole sufficiently so that the threads of the screw head 20 and the plate hole 36 can be aligned. The same driver can then be used to insert the second locking screw into another locking plate hole 36. Again, by adapting the plate for deflection, torque can be minimized to allow the same driver to drive the larger diameter screw at comfortable levels of torque; i.e., not exceeding approximately 15-17 in-lbs. Additional screws can be likewise implanted.

FIG. 10, illustrates the maximum torque at different radial angles for inserting a locking screw into a threaded plate hole with and without the described feet located lateral of the compression holes. As shown, a comfortable threshold for applied torque with a small driver of the type supplied with a disposable surgical kit (e.g., of the type provided with the Biomet ePAK™ system) is approximately 17 in-lbs. The higher line with square points depicts the typical torque necessary to install a 3.5 mm screw as the angle associated with pitch timing misalignment is varied. The lower line with triangle points shows an improvement of 4 to 6 in-lbs of installation torque once the feet have been added adjacent and lateral to the compression screw holes to elevate the plate segment defining the locking screw holes from over the bone. With the reduced installation torque, the system allows implants that need different diameter screws to be comfortably installed with one driver. With for example the long distal radius plate shown in FIGS. 1 to 4, screws with shafts of different diameters may be provided for installation. Reducing the installation torque prevents damage to the screw and bone plate, and prevents potential injury to the patient.

There have been described and illustrated herein embodiments of a bone plate, a disposable surgical kit, and methods of plate implantation. While particular embodiments of the plate, kit and method have been described, it is not intended that the invention be limited thereto, as it is intended that the invention be as broad in scope as the art will allow and that the specification be read likewise. By way of example, while the features herein have been described with respect to a long distal radius plate, other plates including those for placement on the radius bone, as well as other long bones of the extremities, or bones having relatively flat portions, such as the clavicle can be similarly provided with the structure and in a system and as a kit as described. In addition, while various diameter screws are mentioned, such should not in any way limiting on the scope for the screw diameter for the system is intended. By way of example, while 2.7 mm and 3.5 mm locking screws are specifically discussed, it is anticipated that locking screws in diameters of a first diameter 2.5 mm-2.7 mm and a second diameter 3.2 mm to 3.5 mm can be used for distal radius plates, and that other diameters can be used on plates adapted and designed for implantation on other bones. It will therefore be appreciated by those skilled in the art that yet other modifications could be made to the provided invention without deviating from its spirit and scope as claimed.

What is claimed is:

1. A bone plate for use on a bone with a locking screw having a head having a thread with a thread pitch, the bone plate comprising:
    an elongated metal plate having an upper surface, an opposite lower surface for facing the bone, a longitudinal axis extending along the plate, a plurality of compression holes disposed in the plate that are spaced apart along the longitudinal axis, and a plate segment extending between two adjacent compression holes of the plurality of compression holes and having a threaded locking hole disposed therein, wherein each of the plurality of compression holes and the threaded locking hole extend from the upper surface to the lower surface of the plate, wherein each of the plurality of compression holes comprises a pair of lateral sides that are straight, wherein the threaded locking hole comprises a thread with the same thread pitch as, and that matingly corresponds with, the thread of the head of the locking screw, wherein the lower surface of the plate comprises a plurality of pairs of feet extending therefrom, wherein each foot of the plurality of pairs of feet is longitudinally aligned with and laterally displaced relative to the pair of lateral sides of a corresponding one of the plurality of compression holes, wherein each foot of the plurality of pairs of feet comprises a flattened bone-contacting portion extending from a first foot end to a second foot end thereof, and wherein the lower surface of the plate at the plate segment having the threaded locking hole does not have any feet extending therefrom;
    wherein, in use, each of the plurality of the pairs of feet cooperate to displace a lower surface of the plate segment from the bone by a gap such that the plate segment is able to deflect under load of the locking screw by a distance up to the thread pitch so that the thread on the head of the locking screw can be aligned with the thread of the threaded locking hole to reduce the required torque to engage the locking screw into the threaded locking hole; and
    wherein a height of each foot of the plurality of pairs of feet is up to or equal to the thread pitch of the threaded locking hole divided by the number of thread starts of the threaded locking hole.

2. A bone plate according to claim 1, wherein the threaded locking hole comprises a single start thread.

3. A bone plate according to claim 1, wherein the threaded locking hole comprises a double start thread.

4. A bone plate according to claim 1, wherein the threaded locking hole comprises a triple start thread.

5. A bone plate according to claim 1, wherein each foot of the plurality of pairs of feet tapers laterally and longitudinally toward a bone contacting surface of the feet.

6. A bone plate according to claim 5, wherein the length of the bone contacting portion of each foot of the plurality of pairs of feet is substantially parallel to the longitudinal axis of the bone plate and each foot of the plurality of pairs of feet has a width that is substantially transverse to the longitudinal axis of the bone plate, and wherein the length is greater than the width.

7. A bone plate according to claim 1, wherein at least one compression hole of the plurality of compression holes is oblong.

8. A bone plate according to claim 1, wherein the plate is configured for placement on the radius bone.

9. A bone plate according to claim 8, wherein the plate includes a metaphyseal portion and a diaphyseal portion, wherein the plurality of pairs of feet are disposed on the diaphyseal portion.

10. A surgical system, comprising:
    an elongated metal plate having an upper surface, an opposite lower surface for facing bone, a longitudinal axis extending along the plate, a plurality of compression holes disposed in the plate that are spaced apart along the longitudinal axis, and a plate segment extending between two adjacent compression holes of the plurality of compression holes and having a first threaded locking hole disposed therein, wherein each of the plurality of compression holes and the first threaded locking hole extend from the upper surface to the lower surface of the plate, wherein each of the plurality of compression holes comprises a pair of lateral sides that are straight, wherein the first threaded locking hole comprises a thread having a thread pitch, wherein the lower surface of the plate comprises a plurality of pairs of feet extending therefrom, wherein each foot of the plurality of pairs of feet is longitudinally aligned with and laterally displaced relative to the pair of lateral sides of a corresponding one of the plurality of compression holes, wherein each foot of the plurality of pairs of feet comprises a flattened bone-contacting portion extending from a first foot end to a second foot end thereof, wherein the lower surface of the plate at the plate segment having the first threaded locking hole does not have any feet extending therefrom, and wherein each of the plurality of pairs of feet cooperate to displace the plate segment from the bone by a gap;
a plurality of compression screws, each compression screw having a threaded shaft and a head; and
a locking screw having a threaded shaft and a head with an external thread disposed thereon, wherein the external thread has a thread pitch the same as, and that matingly corresponds with, the thread of the first threaded locking hole;
wherein each of the plurality of compression screws are insertable through the compression holes and engageable with underlying bone to compress the bone plate against underlying bone;
wherein, in use, each of the plurality of the pairs of feet cooperate to displace a lower surface of the plate segment from the bone by a gap such that the plate segment is able to deflect under load of the locking screw by a distance up to the thread pitch so that the thread on the head of the locking screw can be aligned with the thread of the first threaded locking hole to reduce the required torque to engage the locking screw into the first threaded locking hole; and
wherein a height of each foot of the plurality of pairs of feet is up to or equal to the thread pitch of the first threaded locking hole divided by the number of thread starts of the first threaded locking hole.

11. The surgical system of claim 10, wherein the first threaded locking hole comprises a single start thread.

12. The surgical system of claim 10, wherein the first threaded locking hole comprises a double start thread.

13. The surgical system of claim 10, wherein the first threaded locking hole comprises a triple start thread.

14. The surgical system of claim 10, further comprising a driver for driving either or both of the plurality of compression screws and the locking screw through the plate and into underlying bone.

15. The surgical system of claim 14, wherein the bone plate, the plurality of compression screws, the locking screw, and the driver are provided in a sterile sealed container.

16. The surgical system of claim 10, wherein the locking screw comprises a first locking screw and further comprising:
a second locking screw having a second diameter that is different than a first diameter of the first locking screw;
wherein the bone plate further comprises a second plate segment extending between a second pair of adjacent compression holes of the plurality of compression holes and having a second threaded locking hole disposed therein, wherein the second threaded locking hole comprises a thread having thread pitch, wherein the second threaded locking hole extends from the upper surface to the lower surface of the bone plate and receives the second locking screw.

17. The surgical system of claim 16, wherein the first diameter is 2.5 mm to 2.7 mm and the second diameter is 3.2 mm to 3.5 mm.

18. The surgical system of claim 10, wherein each foot of the plurality of pairs of feet of the bone plate tapers laterally and longitudinally toward a bone contacting surface of the feet.

19. The surgical system of claim 10, wherein the length of the bone contacting portion of each foot of the plurality of pairs of feet is substantially parallel to the longitudinal axis of the bone plate and each foot of the plurality of pairs of feet has a width that is substantially transverse to the longitudinal axis of the bone plate, and wherein the length is greater than the width.

20. The surgical system of claim 10, wherein at least one compression hole of the plurality of compression holes is oblong.

\* \* \* \* \*